United States Patent [19]
Jauregui et al.

[11] Patent Number: 6,107,043
[45] Date of Patent: Aug. 22, 2000

[54] IMMORTALIZED HEPATOCYTES

[75] Inventors: Hugo O. Jauregui, Providence; Jin Liu, Barrington, both of R.I.

[73] Assignee: Rhode Island Hospital, Providence, R.I.

[21] Appl. No.: 09/246,968

[22] Filed: Feb. 9, 1999

Related U.S. Application Data

[63] Continuation of application No. 08/611,171, Mar. 5, 1996.

[51] Int. Cl.$^7$ ............................... C12Q 1/68; A61F 2/04
[52] U.S. Cl. ................................. 435/6; 435/325; 623/12
[58] Field of Search ........................... 435/6, 325; 623/12

[56] References Cited

U.S. PATENT DOCUMENTS

| | | |
|---|---|---|
| 4,393,133 | 7/1983 | Knowles et al. . |
| 5,290,684 | 3/1994 | Kelly ........................................ 435/29 |
| 5,368,555 | 11/1994 | Sussman et al. . |
| 5,521,076 | 5/1996 | Mulligan et al. ..................... 435/172.3 |
| 5,529,920 | 6/1996 | Cole et al. ................................... 435/6 |
| 5,532,156 | 7/1996 | Talbot et al. ............................. 435/325 |
| 5,665,589 | 9/1997 | Harris et al. ............................. 435/370 |

FOREIGN PATENT DOCUMENTS

WO 91/18087  11/1991  WIPO .

OTHER PUBLICATIONS

Zaret et al, *PNAS*, vol. 85, 1988, pp. 9076–9080.
Orkin et al., *Report and Recommendations of the Panel to Assess the NIH Investment in Research on Gene Therapy*, NIH, 1995.
Pfeifer et al., "Simian virus 40 large tumor antigen–immortalized normal human liver epithelial cells express hepatocyte characteristics and metabolize chemical carcinogens", *Proc. Nat'l. Acad. Sci. USA* 90:5123–5127, (1993).
Pfeifer et al., "Highly efficient establishment of immortalized cells from adult human liver", *Methods of Cell Science*, 17:83–89, (1995).
Raper et al., "Cell Transplantation in Liver–Directed Gene Therapy", *Cell Transplantation*, 2:381–396 (1993).
Roberts et al., "Characterization of Human Hepatocyte Lines Derived from Normal Liver Tissue", *Hepatology*, 19(6), 1390–1399, (1994).
Rozga et al., "A Bioartificial Liver to Treat Severe Acute Liver Failure", *Ann. Surg.* 219:538–546, May 1994.
Seifer et al., "Increased growth of permanent mouse fibroblasts in soft agar after transfection with hepatitis B virus DNA", *Arch Virol*, 126:119–128, (1992).
Sussman et al., "The Artificial Liver", *Scientif. Am. Sci. & Med.*, 68–77, May/Jun. 1995.
Sussman et al., "The Hepatix Extracorporeal Liver Assist Device: Initial Clinical Experience", *Artificial Organs*, 18:390–396 (1994).
Sussman et al., "Letters to the Editor", *Artificial Organs*, 17(1):43–44, (1993).
Willems et al., "Immortalized Human Liver Cell Lines with Phenotypical Characteristics of Hepatoblast and/or Biliary Epithelial Cells: an in vitro Model for the Study of Liver Cell–specific Functions", *Transplantology*, 5:151–59 (1994).

Wilson et al., "Retrovirus–Mediated Transduction of Adult Hepatocytes", *Proc. Natl. Acad. Sci. USA*, 85:3014–18 (1988).
Woodworth et al., "Tumorigenicity of Simian Virus 40–Hepatocyte Cell Lines: Effect of In VItro and In Vivo Passage on Expression of Liver–Specific Genes and Oncogenes", *Molec. and Cell. Biol.*, 8:4492–4501 (1988).
Wu et al., "Establishment and characterization of differentiated, nontransformed hepatocyte cell lines derived from mice transgenic for transforming growth factor α", *Proc. Natl. Acad. Sci. USA*, 91:674–678, (1994).
Zaret et al., "Conditional Enhancement of Liver–Specific Gene Transcription", *Proc. Natl. Acad. Sci. USA*, 85:9076–80 (1988).
Balladur et al., "Transplantation of allogeneic hepatocytes without immunosuppression: Long–term survival", *Surgery*, 117(1):189–194, (1995).
Butterworth et al., "Ammonia: Key Factor in the Pathogenesis of Hepatic Encephalopathy", *Neurochemical Pathology*, 6:1–12 (1987).
Dixit et al., "Repeated Transplantation of Microencapsulated Hepatocytes For Sustained Correction of Hyperbilirubinemia in Gunn Rats", *Cell Transplantation*, 1;275–279 (1992).
Fang et al., "ras Transformation of Simian Virus 40–immortalized Rat Hepatocytes: An in Vitro Model of Hepatocarcinogenesis", *Cancer Research*, 52:173–180, (1992).
Fiers et al., "Complete nucleotide sequence of SV40 DNA", *Nature*, 273:113–120, (1978).
Holmen et al., "Efficient Lipid–Mediated Transfection of DNA into Primary Rat Hepatocytes", *In Vitro Cell Dev. Biol.*, 30:347–51 (1995).
Jauregui et al., "Xenobiotic induction of P–450 PB–4 (IIB1) and P–450c (IA1) and associated monooxygenase activities in primary cultures of adult rat hepatocytes", *Xenobiotica*, 21:1091–1106, (1991).
Miyazaki et al., "Immortalization of Epithelial–like Cells from Human Liver Tissue with SV40 T–Antigen Gene", *Experimental Cell Research*, 206:27–35, (1993).
Muller et al., "Letters to the Editor", *Artificial Organs*, 17(1):44–45, (1993).
Nyberg et al., "Primary Hepatocytes Outperform Hep G2 Cells as the Source of Biotransformation Functions in a Bioartificial Liver", *Ann. Surg.*,220:59–67, (1994).
Paquereau et al., "Electroporation–Mediated Gene Transfer into Hepatocytes: Preservation of a Growth Hormone Response", *Analytical Biochem.*, 204:147–51 (1992).
Kono et al., "Modulation of the Expression of Liver–Specific Functions in Novel Human Hepatocyte Lines Cultured in a Collagen Gel Sandwich Configuration", *Biochem. and Biophys. Res. Commun.*, 220:628–32 (1996).

*Primary Examiner*—James Ketter
*Attorney, Agent, or Firm*—Fish & Richardson, P.C.

[57] ABSTRACT

The invention features a virally-immortalized mammalian hepatocyte, which is derived from a normal liver cell, has differentiated hepatocyte-specific metabolic activity, has the ability to proliferate, and is nontumorigenic after prolonged culture.

19 Claims, 2 Drawing Sheets

IMMORTALIZED HEPATOCYTES

This application is a continuation of U.S. Ser. No. 08/611,171, filed on Mar. 5, 1996, the contents of which is hereby incorporated by reference.

BACKGROUND OF THE INVENTION

The invention relates to immortalized hepatocyte cell lines.

Hybrid extracorporeal liver assist devices (LAD) are a promising therapeutic modality to reduce the potential of hepatic encephalopathy (HE) in patients-with fulminant hepatic failure (FHF) (Sussman et al., 1995, Sci. Am. Science & Medicine May/June 1995:68–77). The exact identity of the toxic metabolites responsible for HE are not clear, but benzodiazepine-like compounds and ammonia have been implicated. The metabolism of benzodiazepines in liver is accomplished by liver-specific cytochrome P450 enzymes.

Two cell based liver support systems have undergone clinical trials in hepatic failure patients. The first device (Sussman et al., 1994, Artif. Organs 18:390–396) contains the cell line C3A (Kelly, J H, WO91/18087) which was subcloned from the hepatoma cell line Hep G2 (Knowles et al., U.S. Pat. No. 4,393,133). The Hep G2/C3A cell line reportedly is tumorigenic. The second device incorporates freshly isolated porcine hepatocytes (Rozga et al., 1994, Ann. Surg. 219: 538–546).

In a study comparing primary hepatocytes to HepG2 cells, the primary cells were superior to the transformed cell in every biotransformation pathway assessed (Nyberg et al., 1994, Ann. Surg. 220:59–67), but primary hepatocytes only transiently provide metabolic functions. Many metabolic activities are rapidly lost in culture.

SUMMARY OF THE INVENTION

The invention features virally-immortalized hepatocytes that retain liver-specific differentiated functions including, but not limited to, phase I oxidative enzymes involved in benzodiazepine metabolism. Such clones can obviate the considerable expense and technical manpower currently required to obtain hepatocytes from large animals to seed liver assist devices. Additionally, these cells can be used in a convenient in vitro method to test liver-specific characteristics as well as to evaluate the toxicity of various compounds.

The invention features a virally-immortalized mammalian hepatocyte which is derived from a normal liver cell, e.g., a porcine hepatocyte, has differentiated hepatocyte-specific metabolic activity and the ability to proliferate, and is nontumorigenic after prolonged culture. By the term "virally-immortalized" is meant being transfected with all or part of the viral genome of a wild type or mutant virus. Preferably the virus is a DNA virus, more preferably the virus is simian virus 40 (SV40). By the term "metabolic activity" is meant the ability to process a potentially toxic compound, e.g., a drug or endogenous metabolite, into a less toxic or non-toxic compound. By the term "normal liver cell" is meant a liver cell which is not derived form a tumor. Preferably, the liver cell is not derived from a transgenic animal. By the term "prolonged passage" is meant greater than about 30 in vitro passages. Preferably the hepatocytes are nontumorigenic after 35 passages, more preferably after 40 passages, more preferably after 45 passages, more preferably after 50 passages, and most preferably after 60 in vitro passages.

The metabolic activity of the hepatocyte preferably includes P450 enzyme activity. P450 enzyme activity includes the ability to metabolize diazepam, lidocaine, and/or 7-ethoxycoumarin (7-EC). The constitutive level of P450 enzyme activity is increased by contacting the hepatocyte with a metabolic inducer. By the term "metabolic inducer" is meant a compound which increases hepatocyte P450 enzyme activity at least 10% compared to the level of activity in the absence of the compound. Preferably, the metabolic inducer increases P450 activity by at least 25%, more preferably by at least 50% compared to the level of activity in the absence of the compound.

The hepatocyte preferably contains a substantially pure SV40 DNA. More preferably, the SV40 DNA encodes the wild type SV40 large T antigen (TAg); most preferably, the DNA encodes the wild type TAg and does not encode other SV40 gene products. TAg expression may be constitutive or inducible. In the latter case, TAg-encoding DNA is operably linked to an inducible promoter, e.g., a dexamethasone (dex)-inducible promoter. The DNA may also encode a temperature-sensitive TAg.

Hepatocytes containing DNA encoding constitutively expressed TAg and hepatocytes containing DNA encoding a temperature-sensitive TAg may also contain a substantially pure tumor suppressor-encoding DNA, e.g., DNA encoding human p53. In preferred embodiments, the substantially pure human p53-encoding DNA is operably linked to a dex-inducible promoter.

"Substantially pure" as used herein refers to a DNA which has been purified from the sequences which flank it in a naturally occurring state, i.e., a DNA fragment which has been removed from the sequences which are normally adjacent to the fragment, e.g., the sequences adjacent to the fragment in the genome in which it naturally occurs, and which has been substantially purified from other components which naturally accompany the DNA, e.g., DNA which has been purified from the proteins which naturally accompany it in the cell.

The invention also features a method of neutralizing a toxic compound, e.g., an endogenous compound such as a metabolite or an exogenously-administered compound such as a drug, in a bodily fluid of a mammal which includes the step of contacting the bodily fluid, e.g., blood or serum, with a virally-immortalized, nontumorigenic, metabolically-active hepatocyte. Preferably, the mammal is a human, more preferably a human suffering from HE. The toxins in the fluid are efficiently processed by the hepatocytes, and thus, the fluid is rendered non-toxic. The processed bodily fluid may then be returned to the patient from which it was derived. For example, the following toxins may be present in bodily fluid taken from a patient and neutralized according to the invention: benzodiazepine, ammonia, 7-EC, lidocaine, and acetaminophen. Contact of the patient-derived bodily fluid with the hepatocytes may take place in any device capable of providing adequate contact of isolated hepatocytes with a bodily fluid, such as a perfusion device, e.g., a LAD or bioreactor.

Virally-immortalized hepatocytes made according to the invention can be transferred to any type of perfusion device for use as the biological component thereof.

The invention also includes a perfusion device which includes (a) a housing defining a perfusion inlet and a perfusion outlet, (b) a porous membrane structure mounted within the housing to define a perfusion compartment and an adjacent hepatocyte compartment, and (c) virally-immortalized, nontumorigenic, metabolically-active mammalian hepatocytes.

Also within the invention is a method of evaluating the toxicity of a compound in vitro which includes the steps of (a) providing a virally-immortalized hepatocyte, (b) contacting the hepatocyte with the compound, and (c) measuring the viability or metabolic activity of the hepatocyte. A decrease in viability or metabolic activity in the presence of the compound compared to that in the absence of the compound indicates that the compound is toxic or is likely to be toxic in vivo.

The invention also includes a method of evaluating the toxicity of a metabolite of a compound which includes the steps of (a) providing a metabolically-active hepatocyte, (b) contacting the metabolically-active hepatocyte with the compound to generate a cell supernatant which may contain a toxic metabolite, (c) removing the cell supernatant from the metabolically-active hepatocyte, (d) providing a virally-immortalized, metabolically-active, nontumorigenic hepatocyte, (e) contacting the immortalized hepatocyte with the supernatant, and (f) measuring the viability or metabolic activity of the immortalized hepatocyte. The hepatocytes of step (a) may include any viable metabolically-active hepatocytes which may or may not be virally-immortalized. For example, if only a short term culture is required to generate the metabolite, primary hepatocytes may be used; if a long term culture is required, immortalized hepatocytes would be required. A decrease in viability or metabolic activity in the presence of the supernatant compared to that in the absence of the supernatant indicates that the compound is toxic or is likely to be toxic in vivo.

Other features and advantages of the invention will be apparent from the following description of the preferred embodiments thereof, and from the claims.

BRIEF DESCRIPTION OF THE DRAWINGS

FIG. 1B is a photograph of a Northern blot. As a control, the filters shown in FIG. 1A were rehybridized with a glyceraldehyde-3-phosphate dehydrogenase (GAPDH) probe to assess loading differences.

DESCRIPTION OF THE PREFERRED EMBODIMENTS

The invention provides immortalized hepatocyte cell lines, established by transfection with a viral transforming agent such as DNA encoding SV40 TAg. The cell lines are nontumorigenic and capable of persistent serial culture while maintaining differentiated liver-specific metabolic activity. Unlike the anchorage-dependent normal primary porcine hepatocytes from which they were derived, these cells require no specific substrates for adhesion and growth. In addition, serum is not necessary either for proliferation or for maintenance of differentiated function.

The cell lines of the invention are classified into five categories. Line I is characterized by constitutive expression of wild type SV40 TAg. Following transfection with wild type SV40 TAg-encoding DNA, transfectants were screened for the ability to proliferate in culture (express SV40 TAg), maintain metabolic activity, in particular the expression of P450 metabolic enzymes such as those required to metabolize diazepam, and maintain other hepatocyte-specific phenotypic characteristics, e.g., cell morphology and expression of hepatocyte-specific cytoskeletal or enzymatic markers. Cell lines can also be screened for other differentiated liver-specific enzymatic activities, e.g., glucuronidation metabolic activity and the ability to metabolize ammonia or other toxic compounds.

In addition to Line I, four other classes of virally-immortalized hepatocyte cell lines (Lines II, III, IV, and V) were developed. To further ensure safety in clinical applications, e.g., human therapeutic use such as cell transplantation, Lines III, IV, and V have been further modified to prevent undesirable proliferation, e.g, tumorigenicity. Proliferative activity and/or metabolic activity are regulatable in each of these cell lines. Regulatable proliferative activity contributes to the safety of these cells lines. For example, Line III is characterized by thermally-regulated (mutant) SV40 TAg expression; Line IV is characterized by constitutively expressed SV40 TAg with dex-inducible p53 expression; and Line V is characterized by thermally-regulated SV40 TAg expression with dex-inducible p53 expression.

Line II which is suitable for in vitro diagnostic use and toxicology testing is characterized by dex-inducible wild type SV40 TAg expression.

Reagents

The following reagents were used in establishment and culture of immortalized hepatocytes:

Chee's essential media (CEM), gentamicin, and fetal bovine serum (FBS) were purchased from GIBCO (Grand Island, N.Y.); insulin was purchased from Eli Lilly (Indianapolis, Ind.); and dex was purchased from Elkins-Sinn (Cherry Hill, N.J.). Vitrogen was obtained from the Collagen Corporation (Palo Alto, Calif.); collagenase from Worthington Biochemical Corporation (Freehold, N.J.). All other chemicals were obtained from Sigma Chemical Co. (St. Louis, Mo.), Aldrich Chemical (Milwaukee, Wis.) or J. T. Baker (Medford, Mass.) unless otherwise noted. Acetaminophen metabolites were obtained from McNeil Pharmaceuticals (Fort Worth, Pa.).

Establishment of immortalized hepatocytes

Five cell lines were developed. Normal primary porcine hepatocytes were transfected with plasmids encoding SV40 TAg (wild type or temperature-sensitive mutant) and the bacterial gene encoding neomycin resistance. SV40 DNA was integrated into the nuclear DNA of the primary porcine hepatoctyes. In some cases, cells were secondarily transfected with DNA encoding a tumor suppressor. Using a lipofection technique, transfection efficiency in porcine hepatocytes was greater than 5%.

For Line I, the cells were transfected with wild-type TAg expressed from a constitutively active promoter/enhancer (SV40 early promoter). Sixty-four initial clones were identified by their ability to proliferate in culture, i.e., form colonies. Twenty-four of those clones were further studied. Twenty-four clones maintained typical hepatocyte morphology and the ability to proliferate in culture. Twenty-three out of twenty-four clones maintained metabolic activity, e.g., the ability to metabolize diazepam. Clone D63 was subcloned based on high P450 metabolic activity as determined by fluorescence activated cell sorting (FACS) analysis. Five subclones (D63A, D63F, D63G, D63H, and D63I) were identified as having high P450 activity.

The cells of Line I showed no evidence of tumorigenicity. Cells were injected into immunocompromised (severe combined immunodeficient (SCID)) mice after 12 passages (P-12); the cells failed to form tumors. In contrast, HepG2 cells under similar conditions formed tumors. Chromosomal analysis revealed that subclone D63H had 35–39 chromosomes after passage 8 (P-8) and 30–38 chromosomes after passage 31 (P-31); normal pig cells have a diploid chromosome number of 38. No gross structural abnormalities were observed. These cells also maintained a range of hepatocyte specific functions and displayed typical hepatocyte intracellular morphology.

Despite their lack of tumorigenicity, an additional mechanism to prevent tumor formation was introduced. For Line IV, a portion of cells from Line I were secondarily transfected with an inducible gene to halt cell proliferation. Highly differentiated clones were selected and transfected with a dex-inducible wild type human p53 gene. Integration of the p53 gene provides a regulatable "on-off" mechanism to control cell proliferation. Because dex induces p53 expression in these cells, any clinical application, e.g., use of an LAD or cell transplantation, that exposes these cells to human blood or serum would (by the presence of dex) prevent proliferative activity.

In Line II, wild type SV40 TAg-encoding DNA is fused to an inducible promoter, mouse mammary tumor virus (MMTV), which favors expression of TAg only in the presence of the inducer, dex. The transfecting plasmid for this line included a MMTV promoter fused to the TAg gene. In this cell line, TAg gene expression (indicative of cell proliferation) is regulated by varying the amount of dex available to the cells. A regulatable transforming gene allows adjustment of the intracellular concentration of the transforming protein. Thus, the cell's ability to proliferate and its differentiation potential can be controlled. For example, in the presence of dex, the cells proliferate, but in the absence of dex, proliferation is reduced or halted and the cells express differentiated liver-specific metabolic activity.

Line III was created by transfection of normal primary porcine hepatoctyes with a temperature-sensitive TAg gene. For the establishment of Line V, selected clones from Line III were secondarily transfected with the wild type human p53 gene. In both Lines IV and V, p53 suppresses TAg. The p53 nucleoprotein gene product inactivates TAg by forming an oligomeric complex with it. Thus, the concentration of intracellular active TAg is manipulated by increasing the relative proportion of inactive (p53-complexed) TAg.

Plasmids

Line I which constitutively expresses wild type SV40 TAg was created by transfecting primary hepatocytes with DNA encoding wild type SV40 TAg (Fiers et al., 1978, Nature 273:113–120, hereby incorporated by reference). The source of the wild type TAg was pBR/SV (ATCC #45019). The pBR/SV plasmid contains the entire SV40 genome inserted in the BamHI site of pBR322. The initial construct containing a KpnI-BamHI fragment from pBR/SV encompassing the SV40 promoter and the entire early region, was inserted into KpnI and Bam HI-digested Bluescript S-K (Stratagene, La Jolla, Calif.). The resulting construct, Blue-TAg, contains the SV40 promoter-T antigen fragment.

Line II which inducibly expresses SV40 TAg was created by transfecting primary hepatocytes with DNA encoding wild type SV40 TAg under the control of the dex-inducible MMTV promoter. The AvrII-BamHI fragment of SV40, containing the early region and lacking the viral promoter, was blunt-ended and ligated into SalI-digested, blunt-ended pMAMneo. The latter contains a hybrid long terminal repeat (LTR) which contains the Rous Sarcoma Virus (RSV) enhancer and dex-inducible MMTV promoter. Correct orientation of the insert in the resulting plasmid, pMAMneo-$SV_T$, was confirmed by restriction analysis.

Line III which expresses a temperature-sensitive SV40 TAg was created by transfecting primary hepatocytes with DNA encoding a mutant SV40 TAg ($SV40^{ts}A58$). DNA encoding the temperature-sensitive SV40 TAg has a mutation within the SV40 A gene (Jat et al., 1989, Mol. Cell Biol. 9:1672–1681). At 33° C., the cells proliferate and express SV40 TAg but have low liver-specific differentiated functions. At 39° C., the cells cease proliferation and express liver-specific functions such as metabolic activity.

Lines IV and V were created by secondarily transfecting cells from Lines I and III respectively with DNA encoding the tumor suppressor, p53. The gene encoding human p53 (tumor suppressor) was obtained from the American Type Culture Collection (ATCC) as a 2 kb cDNA insert in pBR322 (php53B; ATCC #57254). The fragment, between NheI and SalI restriction enzyme sites which contains wild type p53 gene from php53B was inserted into Nhe1-SalI digested pMAM resulting a new construct, pMAM-p53.

Transfection Method

Porcine hepatocytes were isolated and established in culture by known methods. Transfection of normal primary porcine hepatocytes was carried out as follows. Freshly isolated porcine hepatocytes were seeded $2 \times 10^6$ cells/dish and maintained in standard CEM medium supplemented with 10% FBS (10% FBS-CEM) overnight (1-day culture). The 10% FBS-CEM media of the 1-day cultures were replaced with 5% FBS-CEM. For Line I, Blue TAg (6.4 $\mu$g) plus pRSVneo (1.6 $\mu$g) (molar ratio 5:1) were dissolved in 200 $\mu$l OPTI-MEM (GIBCO/BRL, Gaithersburg, Md.). For Line II, the plasmid pMAMneo/$SV_T$ (5 $\mu$g) was dissolved in 200 Al OPTI-MEM (GIBCO/BRL). For Line III, the plasmid encoding temperature-sensitive SV40 TAg (9 $\mu$g) plus 1 $\mu$g of pRSVneo (molar ratio 5:1) were dissolved in 200 $\mu$l of OPTI-MEM (GIBCO/BRL). The plasmid-medium from Lines I-II was then combined with 200 $\mu$l OPTI-MEM which contained 20 $\mu$l of LIPOFECTIN® reagent (GIBCO/BRL) and incubated at room temperature for 20 min. Following incubation, this mixture was gently added to the porcine hepatocyte cultures.

The transfectants of Lines I & II were incubated for 6 hours at 37° C., and the transfectants of Line III were incubated for 6 hours at 33° C. (the temperature at which the cells proliferate). The DNA-containing medium was replaced with 10% FBS-CEM, and the transfectants were cultured for 5 days, during which the media was replaced every 48 hours.

Selection of transfected cells

Successfully transfected cells contained both TAg and the bacterial neomycin-kanamycin resistance gene, neo. The addition of G418 (GIBCO/BRL) to the culture medium killed any cells which had not integrated the neo gene within 10 days. Cells which contained the neo gene (but not TAg-encoding DNA) died as is typical of primary cultured cells.

Transfected cells were selected by the addition of G418 (12.5 mg/ml media). After G418 selection was terminated, the transfected cells grew and formed colonies. Single clones were transferred to fresh dishes and maintained in culture.

Successful transfection of the cells with TAg-encoding DNA was confirmed by standard Northern blot analysis to detect the presence of SV40 TAg mRNA.

Secondary transfection

Subconfluent cultures of cells from Line I or III derived from an early passage were subjected to a secondary transfection. The medium of the culture of Line I or III was replaced with 5% FBS-CEM. Plasmid pMAMneo/p53 (10 $\mu$g) was added to 200 $\mu$l OPTI-MEM, and LIPOFECTIN® reagent (20 $\mu$l) was added to 200 $\mu$l OPTI-MEM. The plasmid and lipofection reagent solutions were then combined and incubated at room temperature for 20 min. Following incubation, a 200 µl aliquot was added to each culture plate of line I or III. For Line I, cultures were incubated at 37° C. for 6 hours, and for Line III, they were incubated at 33° C. for 6 hours. The medium of each of the cultures was then replaced with 10% FBS-CEM. The cells of Line I were cultured at 37° C. for 3 days, and the cells of Line III were incubated at 33° C. for 3 days. After the 3-day culture, the cells were divided yielding approximately $1 \times 10^6$ cells per culture plate. For Line I, the cells were incubated for 7–10 days in modified CEM media (dex-free) at 37° C., and for Line III, the cells were incubated for 7–10 days in modified CEM media at 33° C. Single clones were transferred to individual dishes.

Immortalized cells can be further transfected with additional genes, e.g., those encoding absent or defective gene products, prior to use as a human therapeutic in order to compensate for absent or defective gene products in a human patient.

Selection of cells with P450 enzyme activity

The formation of fluorescent products from a non-fluorescent substrate, 5.6-methoxycarbonylfluorescein, by hepatocytes via the P450 metabolic pathway was used as the basis for FACS to identify and concentrate a population of immortalized hepatocytes with high P450 enzyme activity.

Hepatocytes were labeled with 5.6-methoxycarbonylfluorescein as follows. Cultured cells were washed with phosphate buffered saline-pH 7.4 (PBS) and plated on tissue culture plates. The substrate solution was prepared by adding 5.6-methoxycarbonylfluorescein (Molecular Probes, Eugene, Oreg.), to PBS to a final concentration of 100 µM/L. The substrate solution (5 ml) was added to the washed plated cells. The plates containing cells and substrate solution were incubated in darkness at 37° C. for 15 min. and then washed with PBS. For FACS analysis, the cells were removed from the culture plates by trypsin digestion and resuspended in 10% FBS-CEM supplemented with antibiotics. The cell suspension was then subjected to FACS analysis or stored at 4° C. until FACS analysis.

FACS analysis was performed using the Becton Dickinson (Rutherford, N.J.) FACSort machine. The 486 nm line of an argon laser was used for fluorescence excitation. Emission was measured using a 520–560 nm bandpass filter. Fluorescent cells were deemed to be positive for P450 activity. The brightest fluorescent cells (e.g., the top 5% of the cells) were sorted into 50 ml tubes containing medium. Weakly fluorescent cells were discarded.

Cells with P450 activity were centrifuged for 20 min. at 7×g, resuspended in medium, and plated in tissue culture dishes.

Immunofluorescent staining

To characterize the cell type of the immortalized cells, immunofluorescent staining was carried out using anti-keratin-8 and anti-keratin-18 antibodies. These antibodies bind to hepatocytes hut not other liver cells, such as fibroblasts, Ito cells, smooth muscle cells and bile duct cells.

A cell sample was fixed with absolute acetone and then stained with hepatocyte-specific antibodies as follows. The cells were cytospun onto pretreated slides (Superfrost/plus, Fisher Scientific, Pittsburgh, Pa.) and incubated with mouse anti-keratin-8 and mouse anti-keratin-18 (Amersham, Arlington Heights, Ill.) for 30 min. at 37° C. After rinsing with PBS, bound immunoglobulin (IgG) was detected by further incubation for 30 min. with fluorescein isothiocyanate (FITC)-conjugated goat globulins directed against mouse IgG (Sigma, St. Louis, Mo.). The slides were stained with propidium iodide (Sigma) to show nuclei.

Evaluation of metabolic activity

P450 metabolic activity (e.g., diazepam metabolism, lidocaine metabolism, 7-EC metabolism and dealkylase activity) and glucuronidation activity (e.g., acetaminophen metabolism) were analyzed as follows. Substrates were added to hepatocyte cultures (diazepam (50 µg/ml); 7-EC (50 µg/ml); and acetaminophen (5 mM; 0.75 mg/ml) and incubated for 3 hours prior to evaluating viability and/or metabolic activity. A media control was incubated simultaneously under similar conditions in the absence of cells. Thymidine incorporation by cultured hepatocytes was measured to assess cell proliferation in vitro. Media from cell cultures, i.e., culture supernatants, were collected and stored at −30° C. until assayed. After removal of the culture supernatants, the culture plates were rinsed 3 times with phosphate buffered saline (PBS) and reserved for protein determination by known methods, e.g., Hayner et al. 1982, Tissue Culture Methods 7:77–80.

Diazepam metabolic activity was measured as follows. $4 \times 10^6$ cells were cultured in a monolayer in 5 ml of medium containing 50 µg/ml diazepam, and the amount of diazepam metabolites present in the culture supernatant measured after 3 hours of culture. Diazepam metabolites were assayed by high performance liquid chromatography (HPLC) using a C18 µ-Bondpack reverse phase column according to known methods, e.g., Jauregui et al., 1991, Xenobiotica 21:1091–1106.

7-EC metabolism was measured as follows. $4 \times 10^6$ cells were cultured in a monolayer in 5 ml of medium containing 50 µg/ml 7-EC, and the amount of 7-hydroxycoumarin present in the culture supernatant measured after 3 hours of culture. 7-hydroxycoumarin levels were assayed using a C18 µ-Bondpack reverse phase HPLC column according to known methods, e.g., Jauregui et al., 1991, Xenobiotica 21:1091–1106.

Acetaminophen and its metabolites were determined by ion-pairing HPLC using a C18 reverse phase column. Acetaminophen metabolism was measured as follows. $4 \times 10^6$ cells were cultured in a monolayer in 5 ml of medium containing 5 mM acetaminophen (0.756 mg/ml), and the amount of acetaminophen glucuronide present in the culture supernatant measured after 3 hours of culture. Acetaminophen and its metabolites, e.g., acetaminophen glucuronide, were determined by ion-pairing high performance liquid chromatography, e.g, using the method of Colin et al., 1986, J. Chromatogr. 377:243–251. Acetaminophen may also be metabolized via a sulfonation pathway; metabolites may be assayed using methods known in the art.

Lidocaine metabolism is measured using known methods, e.g., Jauregui et al., 1995, Hepatology 21:460–469. For example, $4 \times 10^6$ cells were cultured in a monolayer in 5 ml of medium containing 20 µg/ml lidocaine, and the amount, of lidocaine metabolite, e.g., monoethylglycinexylidide (MEGX) present in the culture supernatant is measured after 3 hours of culture. Metabolism of lidocaine is tested using a TDX Analyzer manufactured by Abbott Diagnostics Laboratories, No. Chicago, Ill.

Ammonia metabolism is also measured according to methods known in the art, e.g., using the commercial analyzer, Ektachem, manufactured by Kodak Corp. Rochester, N.Y. Ammonia metabolism is detected by measuring the amount of ammonia remaining in the culture supernatant after 3 hours of culture.

Characterization of immortalized hepatocytes

Normal primary porcine hepatocytes were transfected with SV40 DNA to create immortalized cells. Stable cell lines were selected and maintained for more than 40 passages. Immortalized hepatocytes maintain differentiated liver-specific functions such as metabolic activity, in particular P450 enzyme activity (e.g, diazepam metabolism (TABLE 2), lidocaine metabolism, 7-EC metabolism (TABLE 3), and dealkylase activity (TABLE 1)) and glucuronidation activity (e.g., acetaminophen metabolism (TABLE 4)).

TABLE 1

Fluoresceins of mixed function oxidase in porcine hepatocytes D clone

| | | | |
|---|---|---|---|
| D1 | ++ | D11#1 | ++++ |
| D2 | ++ | D11#2 | ++++ |
| D3 | + | D41 | +++ |
| D4 | ± | D46 | ++++ |
| D6 | +++ | D54 | ++ |
| D7 | + | D61 | ++ |
| D8 | ± | D63 | ++++ |
| D9 | ++ | D64 | + |
| D10 | ± | D58 | ± |
| D12 | ++ | | |
| D13 | ± | | |
| D14 | ++ | | |
| D15 | ++ | | |
| D16 | + | | |

5,6, methoxycarbonylfluorescein is a substrate of p450 dealkylase

TABLE 2

Diazepam Metabolic Activity of Porcine Hepatocyte Clones
($\mu$g total diazepain metabolites/mg cell protein)

| Passage | D 63 A | D 63 F | D 63 G | D 63 H | D 63 I | Notes |
|---|---|---|---|---|---|---|
| 6 | 19.71 | 23.95 | 4.46 | 5.41 | 15.31 | |
| 7 | 12.66 | 13.94 | 12.59 | 4.59 | 17.52 | |
| 9 | 22.13 | 20.38 | 18.42 | 7.59 | 22.21 | |
| 11 | 22.56 | 30.54 | 26.84 | 8.78 | 36.84 | |
| 12 | 1.39 | 1.61 | 1.74 | 0.00 | 1.78 | #1) 10% FBS only |
| " | 10.37 | 9.60 | 11.22 | 3.80 | 11.99 | #2) 10% FBS + rifampin (non-coated plates) |
| " | 12.86 | 13.53 | 12.56 | 4.51 | 12.30 | #3) 10% FBS + rifampin |
| 13 | 3.60 | 7.42 | 0.00 | — | 3.77 | #1) Rifampin + 0% FBS |
| " | 11.86 | 11.31 | 7.24 | — | 7.04 | #2) Rifampin + 10% FBS |
| " | 0.00 | 0.00 | 0.00 | — | 0.00 | #3) 0% FBS only |
| " | 0.85 | 0.83 | 1.22 | — | 0.92 | #4) 10% FBS only |
| " | 2.68 | 4.23 | 0.00 | — | 0.00 | #5) Rifampin + 0% FBS (non-coated plates) |
| " | 10.82 | 9.90 | 7.71 | — | 6.22 | #6) Rifampin + 10% FBS (non-coated plates) |
| 15 | 8.51 | 12.88 | 4.57 | 0.00 | 4.35 | |
| 17 | 14.78 | 12.87 | 8.88 | 15.63 | 10.48 | |
| 18 | 13.15 | 6.63 | 20.63 | 16.59 | 3.72 | |
| 19 | 16.56 | 13.35 | 16.40 | 16.26 | 10.74 | |
| 20 | 26.88 | 21.06 | 21.58 | 37.72 | 27.26 | |
| 21 | 5.30 | 19.26 | 10.51 | 18.03 | 11.36 | |
| 22 | 0.00 | 10.53 | 6.69 | 31.54 | 4.78 | |
| 23 | 0.00 | 6.56 | 5.01 | 13.05 | 0.00 | |
| 24 | 4.67 | 5.51 | 7.99 | 25.95 | 6.78 | |
| 25 | 0.00 | 14.16 | 17.80 | 41.44 | 0.00 | |
| 26 | 0.00 | 6.24 | 0.00 | 16.07 | 7.74 | |
| 27 | 0.00 | 5.86 | 0.0/1.68 (6-1) | 0.00 | 0.00 | |
| 30 | 0.00 | 6.89 | 10.12 | 26.39 | 27.43 | |
| 31 | 0.00 | 7.93 | 7.67 | 16.47 | 32.15 | |
| 32 | — | 16.42 | 13.86 | — | 24.53 | |
| 33 | — | — | — | 31.22 | — | |
| 33 | — | 1.70 | 2.25 | 30.09 | 0.00 | |
| 34 | 0.00 (P-33) | 15.52 | 8.84 | 19.40 | 26.99 | |
| 35 | — | 2.63 | — | — | 10.87 | |
| — | — | — | 3.15 | 30.36 | — | |
| — | — | 5.19 (P-36) | 5.56 (P-34) (P-35) | 48.20 (P-36) (P-37) | 15.12 (P-36) | |
| — | — | 14.24 (P-37) | 7.74 (P-36) | 12.80 (P-38) | 27.23 (P-37) | |
| — | 0.00 (P-36) | 11.00 (P-38) | 9.67 (P-37) | 26.90 (P-39) | 25.38 (P-38) | |
| — | 0.00 (P-38) | 14.90 (P-42) | 10.23 (P-41) | 8.97 (P-43) | 23.71 (P-42) | |

Table 3

Metabolism of 7-Ethoxycoumarin in Porcine Hepatocyte Clones Seeded on Lux Permanox Dishes

EXPERIMENT #1

| Sample | 7-Hydroxycoumarin ($\mu$g/ml) | T-Protein (mg) | $\mu$g/mg protein |
|---|---|---|---|
| D 63 F P-42 | 0.58 | 3.55 | 0.82 |
| D 63 G P-41 | 0.91 | 3.63 | 1.25 |
| D 63 I P-42 | 1.69 | 3.70 | 2.28 |

EXPERIMENT #2

| Sample | 7-Hydroxycoumarin ($\mu$g/ml) | T-Protein (mg) | $\mu$g/mg protein |
|---|---|---|---|
| D 63 H P-43 | 0.38 | 3.23 | 0.59 |

*Clones were incubated with 50 $\mu$M 3-methylcholanthrene for 72 hours prior to 7-EC incubation Table 4

Acetaminophen Glucuronide Production in Porcine Hepatocyte Clones Seeded on Lux Permanox Dishes

EXPERIMENT #2

| Sample | Acetaminophen glucuronide $\mu$g/ml |
|---|---|
| D 63 P-8 | 5.7 |

EXPERIMENT #2

| Sample | Acetaminophen glucuronide $\mu$g/ml |
|---|---|
| D 63 P-8 | 5.7 |

EXPERIMENT #3

| Sample | Acetaminophen glucuronide (μg/ml) | T. Protein (mg) | μg/mg protein |
|---|---|---|---|
| D 63 F P-42 | 20.28 | 3.78 | 26.83 |
| D 63 G P-41 | 24.88 | 3.54 | 35.14 |
| D 63 I P-42 | 31.45 | 3.70 | 42.50 |

EXPERIMENT #4

| Sample | Acetaminophen glucuronide (μg/ml) | T. Protein (mg) | μg/mg protein |
|---|---|---|---|
| D 63 H P-43 | 37.38 | 3.53 | 52.95 |

At low plating density (less than $0.5 \times 10^6$ cells per 21 cm$^2$ dish), the cells proliferate and exhibit low levels of differentiated liver-specific functions. However, as the cultures reach confluence (e.g., at 50% confluence), the cells express differentiated liver-specific functions and become responsive to metabolic inducers. P450 metabolic activity is constitutively expressed and induced to a higher level of expression and/or activity by a variety of metabolic inducers. Metabolic inducers include polycyclic aromatic hydrocarbons (e.g., benzo[a]pyrene, 2,3,7,8-tetrachlorbenzo-p-dioxin; TCDD), isosafrole, omeprazole, phenobarbitol, methylcholanthrene, alcohol, acetone, pyrazole, imidazole, rifampin, glucocorticoids, miconazole, erythromycin and other macrolide antibiotics, peroxisome proliferators (e.g., clofibrate, phthalate esters, and halogenated hydrocarbon solvents). For example, metabolic inducers, e.g., rifampin, phenobarbitol and methylcholanthrene, introduced into a low density culture of immortalized cells inhibited proliferation and actually increased cell death. When the same metabolic inducer was introduced to cells cultured at higher density, the cells showed increased metabolic activity without significant cell death. The cell lines have been grown in quantity in flasks and roller bottles with or without microcarriers or protein substrates (TABLE 5).

The immortalized cell lines also retain many other characteristics of normal primary hepatocytes. Immunocytochemical staining revealed the presence of carbamyl phosphate synthetase, an early enzyme of the urea cycle. The immortalized cells also stained positively for cytokeratin 8 and cytokeratin 18, hepatocyte-specific cytoskeletal proteins. Electron microscopic evaluation revealed that the cells retained morphologic characteristics of normal hepatocytes. These data indicate that the immortalized cells retain hepatocyte-specific phenotypic markers.

Figure 1A:
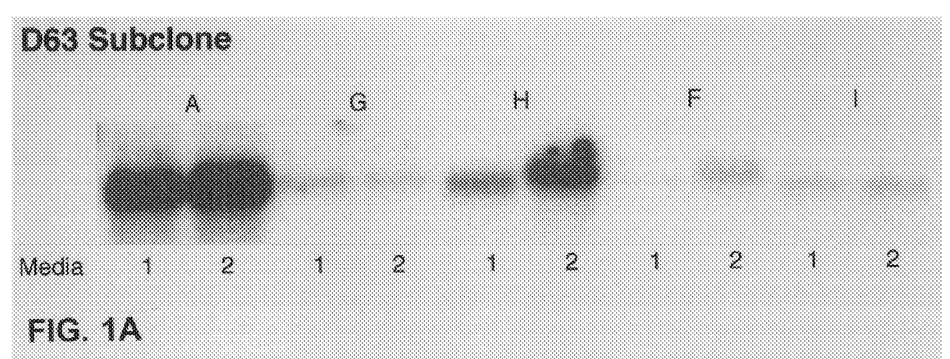
FIG. 1A is a photograph of a Northern blot showing SV40 TAg gene transcription in subclone D63 in the absence of a metabolic inducer (lanes labeled "1") and in the presence of a metabolic inducer (lanes labeled "2").
Figure 1B:
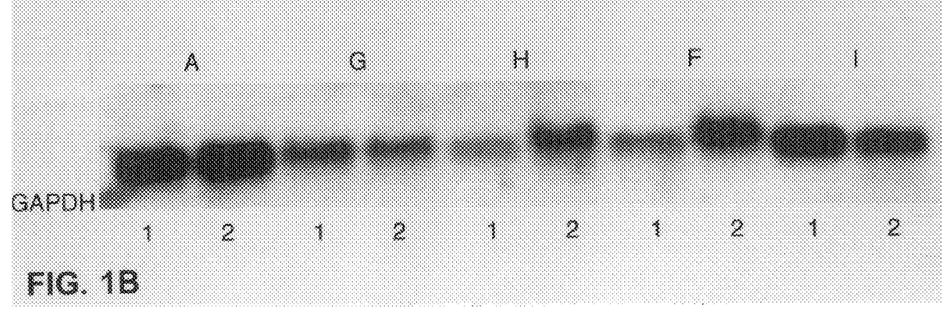

The cells were also stained for the presence of SV40 TAg. Each of the cell lines stained positively for SV40 TAg confirming the integration of SV40 DNA into nuclear DNA of the immortalized cell. Northern blot analysis confirmed the presence of TAg mRNA (FIGS. 1A and 1B).

Use

The immortalized cells metabolize substances implicated in HE (an often fatal complication of acute hepatic failure). These cells are therefore useful as the biological component of a LAD.

The cell lines can also be used in (i) intra-corporeal hepatic therapy (cell transplantation), (ii) in vitro toxicology testing, and (iii) hepatocyte function studies. Cell lines I, III, IV and V are suitable and safe for clinical applications because their proliferation can be controlled, i.e., halted, in clinical in vivo settings. Cell line II is suitable for in vitro diagnostic assays and toxicology testing.

Structure of Perfusion Device

Figure 2:
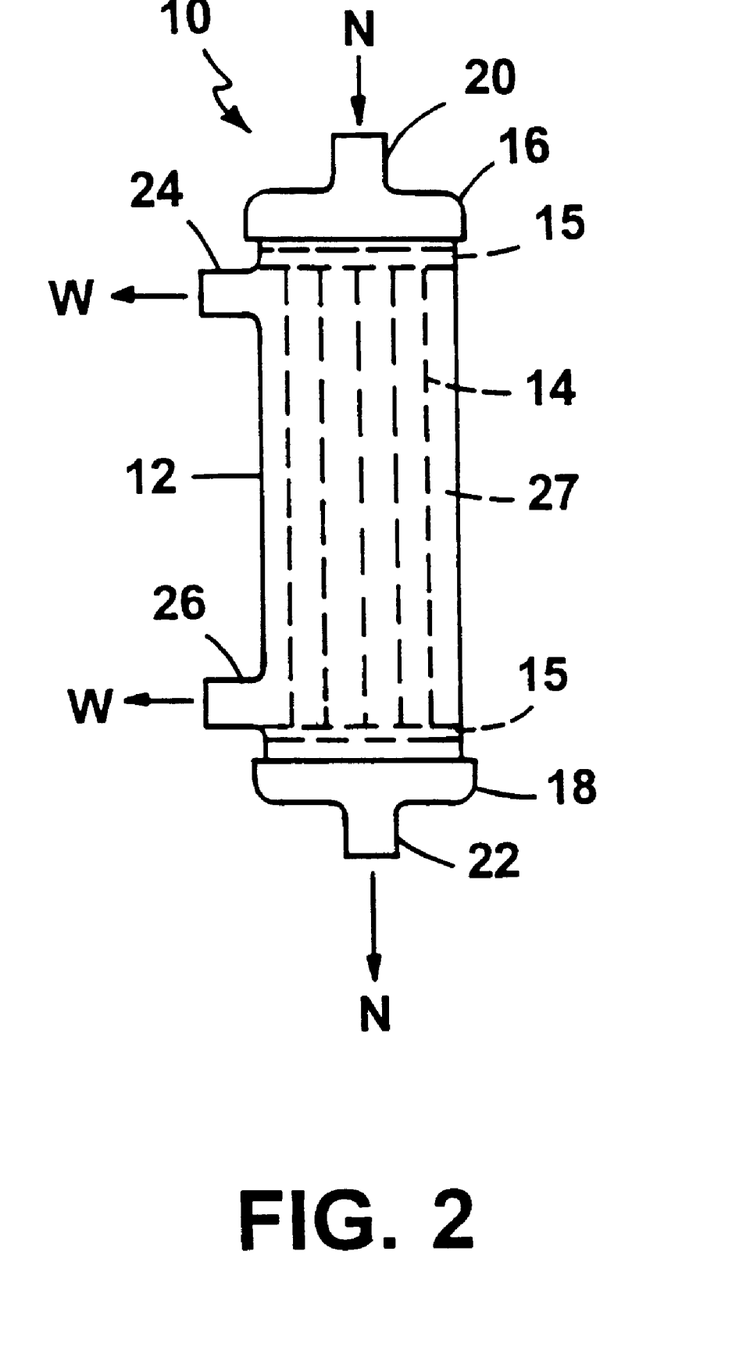
FIG. 2 is a diagram of a perfusion device.

FIG. 2 shows a perfusion device. The device includes a rigid, plastic outer shell 12, a plurality of hollow semi-permeable membrane fibers 14 therein, and outer caps, 16 and 18. Fibers 14 are porous fibers. The upper and lower ends of hollow fibers 14 are potted in potting material 15 and thereby sealed to the inner surface of shell 12 near the upper and lower ends, employing techniques which are well known in the art. Cap 16 has perfusion inlet 20, and cap 18 has perfusion outlet 22, both of which communicate with the interiors of hollow fibers 14. Ports 24 and 26 are inward of potting 15 and provide access to the region within container 12 external of hollow fibers 14. Fibers 14 act as a barrier between perfusion compartment 25, inside of the fibers 14 and hepatocyte compartment 27, in the region between the exterior surfaces of fibers 14 and the inside of shell 12.

Artificial liver 10 is made from a standard shell provided with potted hollow fibers according to procedures well known in the art. Fibers 14 are made of membranes which include but are not limited to polyacrylic polyurethane, cellulose acetate or polysulfone polymer, have outer diameters between 150 μm and 400 μm, have inner diameters between 50 μm and 350 μm, and have pores of a size to have molecular weight cutoffs of 40,000 to 250,000 daltons. The outer surfaces of fibers 14 may be treated, e.g., by treatment of the fibers with collagen, lectin, laminin, or fibronectin, or left untreated for the attachment of immortalized cells. The perfusion device may be regenerated by removing the hepatocytes from the hepatocyte compartment and replenishing the compartment with a fresh aliquot of immortalized hepatocytes.

Toxicology Testing

Immortalized hepatocytes may also be used as a screening tool to evaluate the toxicity of a compound, e.g., a drug to be administered to a patient or a metabolite of such a drug. The in vitro assay includes the following steps: providing a sample of immortalized hepatocytes;

contacting the sample with the compound to be tested, e.g., for at least 15 min.; and measuring the viability of the sample. Some compounds may require contacting the hepatocytes for longer than 15 min., e.g., 1 hour, 3 hours, 24 hours, or up to several days, in order to determine the effect of the compound on the hepatocytes. Viability of the cells may be measured by staining the cells with a vital dye such as trypan blue, or detecting lactate dehydrogenase (LDH) leakage. Alternatively, propidium iodide staining can be used to assess cell viability. A decrease in viability of the hepatocytes in the presence of the test compound compared to that in the absence of the same compound indicates that the compound is or is likely to be toxic in vivo. Alternatively, rather than measuring cell viability following contact with the test compound, metabolic activity of the cells may be measured. In this case, a decrease in metabolic activity, e.g, the ability to metabolize diazepam, in the presence of the test compound compared to that in the absence of compound indicates that the compound impairs the enzymatic function of the liver, and therefore, is or is likely to be toxic in vivo.

Some compounds, e.g., drugs administered to a patient, are not toxic upon administration but are subsequently metabolized into a toxic metabolite, which in turn may impair the function of liver cells or other cells and/or cause cell death. Thus, the invention, includes an in vitro toxicology assay to evaluate the toxicity of metabolites of test compounds. The method includes the steps of: providing a metabolically-active hepatocyte; contacting the metabolically-active hepatocyte with a test compound to generate a cell supernatant; removing the cell supernatant from the metabolically-active hepatocyte; providing a virally-immortalized, metabolically-active, nontumorigenic hepatocyte; contacting the virally-immortalized hepatocyte with the supernatant; and measuring the viability of the immortalized hepatocytes. As above, some compounds may require contacting the hepatocytes with the compound or supernatant, respectively, for longer than 15 min., e.g., 1 hour, 3 hours, 24 hours, or up to several days, in order to generate a toxic metabolite or to determine the effect of the compound on the indicator hepatocytes, respectively. Any viable metabolically-active hepatocytes may be used to generate the cell supernatant. For example, primary hepatocytes can be used if only a short term culture is required to generated the metabolite to be tested. For longer culture times, e.g., several days, virally-immortalized hepatocytes are used. Virally-immortallized hepatocytes are the indicator hepatocytes, i.e, the hepatocytes which will be evaluated for viability and/or metabolic activity. A decrease in viability of the indicator hepatocytes in the presence of the supernatant compared to that in the absence of the supernatant indicates that the test compound is or is likely to be toxic in vivo. Alternatively, rather than measuring the viability of the indicator hepatocytes, their metabolic activity can be measured as described above. In this case, a decrease in the level of metabolic activity in the presence of the supernatant compared to that in the absence of the supernatant indicates that the test compound is or is likely to be toxic in vivo.

Cell transplantation

Immortalized cells can be transplanted into individuals in need of liver support functions, e.g., those suffering from HE. For example, to minimize transplant rejection, the cells can be encapsulated in a membrane which permits exchange of fluids but prevents cell/cell contact. Transplantation of microencapsulated hepatocytes is known in the art, e.g., Balladur et al., 1995, Surgery 117:189–194; and Dixit et al., 1992, Cell Transplantation 1:275–279.

Immortalized hepatocytes may also be transfected with DNA encoding a human gene product which is absent or defective using known methods, e.g., Raper et al., 1993, Transplantation 2:381–400. Such cells may be transplanted into the affected individual to produce the recombinant gene product in vivo.

Advantages

The immortalized hepatocytes described are unique in that they maintain differentiated liver-specific metabolic activity concurrent with proliferative activity. Typically, as differentiation progresses, proliferation diminishes (Freshney, R I, 1987, Culture of animal cells: A manual of basic technique, 2nd ed., New York, N.Y., Alan R. Liss, Inc. p. 187). Except in tumor cells, long-term maintenance of these functions are incompatible. The immortalized hepatocyte cell lines of the invention exhibit a range of liver-specific functions and are nontumorigenic when injected into SCID mice.

A major advantage of the cell lines of the invention is their lack of tumorigenicity, even after prolonged culture. A number of additional safety measures have been engineered into nontumorigenic cells of Line I in order to make them even safer for clinical use, particularly in vivo therapeutic use. For example, Line III expresses a temperature-sensitive SV40 TAg which is non-functional at physiologic temperatures, and Lines IV and V express a dex-inducible tumor suppressor, human p53.

The cells can be produced in quantities adequate for commercial usage and are not dependent on extracellular matrix proteins or other substrates, e.g., collagen, lectin, laminin, or fibronectin, for surface adhesion or activity (TABLE 5) which allows a greater variety of biomaterials to be considered for LAD design. The need for collagenase is obviated. The reduced need for serum supplementation also decreases commercial costs.

TABLE 5

Diazepam Metabolite Production

|  | Vitrogen Coated | Non-Coated |
| --- | --- | --- |
|  | 15.2 | 14.1 |
| CEM + 2% FBS | 19.5 | 16.1 |
| CEM + 5% FBS | 21.17 | 19.3 |
| CEM + 10% FBS | 21.1 | 19.4 |

Freshly isolated hepatocytes and hepatoma-derived cells have been used as the biological component of LADs. Neoplastic cell lines may not provide all necessary metabolic functions and are potentially risky to use in devices that are in contact with the patient's bloodstream. However, the provision of a continuous supply of primary or freshly isolated hepatocytes from large animals to seed LAD involves expensive procedures and maintenance of large animal colonies. Freshly isolated porcine hepatocytes have been shown to have greater biotransformation capacity than the HepG2/C3A cell line, but the use of fresh primary cells presents logistical problems (i.e., on call surgical personnel and facilities, animal access and transportation/storage needs). The cell lines described herein have equivalent or higher P450 activity than cryopreserved primary cells. For example, both cell of Line I and fresh hepatocytes produce about 37 Ag diazepam metabolites/mg protein; cryopreserved cells produce about 30 µg/mg protein. The immortalized cell lines of the invention can be frozen at −80° C. or in liquid nitrogen for indefinite periods without loss of activity (TABLE 6). Given the ease of storage and maintenance of activity of the immortalized hepatocyte, on demand delivery of a medical device containing these cells is possible. LADS which utilize immortalized hepatocytes present no greater demands for usage than the technology common to kidney dialysis programs.

TABLE 6

CELL LINE I

| Storage | Time (days) | Diazepam metabolites µg/mg protein |
| --- | --- | --- |
| 4° | 1 | 32.88 |
| 4° | 3 | 25.90 |
| −80° | 14 | 36.26 |
| −30° | 1 | 22.20 |
| dry ice | 1 | 28.63 |
| dry ice | 2 | 21.05 |

Immortalized hepatocytes also form the basis of an improved toxicology assay. Toxicology testing has typically been performed in vivo. In many cases, the metabolic pathways of the animals used differ considerably from those of the human. Additionally, there is increasing public concern over the use of animals for toxicity studies creating a need for alternative methods of drug screening. The hepatocyte cell lines described herein provide an alternative to conventional in vivo toxicology testing.

Other embodiments are within the following claims.

What is claimed is:

1. A virally-immortalized mammalian hepatocyte, said hepatocyte
   (a) being derived from a normal liver cell;
   (b) having differentiated hepatocyte-specific metabolic activity; and
   (c) having the ability to proliferate, wherein said hepatocyte is nontumorigenic after prolonged culture and wherein serum is not required for proliferation in prolonged culture.

2. The hepatocyte of claim 1, wherein said metabolic activity comprises P450 enzyme activity.

3. The hepatocyte of claim 2, wherein said P450 enzyme activity is increased by contacting said hepatocyte with a metabolic inducer.

4. The hepatocyte of claim 1, wherein said hepatocyte comprises substantially pure simian virus 40 (SV40) DNA.

5. The hepatocyte of claim 4, wherein said DNA encodes wild type SV40 large T antigen (TAg).

6. The hepatocyte of claim 5, wherein expression of said TAg is constitutive.

7. The hepatocyte of claim 5, wherein expression of said TAg is inducible.

8. The hepatocyte of claim 7, wherein said expression is induced by dexamethasone.

9. The hepatocyte of claim 4, wherein said DNA encodes a temperature-sensitive TAg.

10. The hepatocyte of claim 6, wherein said hepatocyte further comprises a substantially pure tumor suppressor-encoding DNA.

11. The hepatocyte of claim 9, wherein said hepatocyte further comprises a substantially pure tumor suppressor-encoding DNA.

12. The hepatocyte of claim 10 or 11, wherein said hepatocyte comprises a substantially pure human p53-encoding DNA.

13. A method of evaluating the toxicity of a compound in vitro, comprising
   (a) providing a metabolically-active hepatocyte;
   (b) contacting said metabolically-active hepatocyte with said compound to generate a cell supernatant;
   (c) removing said cell supernatant from said metabolically-active hepatocyte;
   (d) providing the hepatocyte of claim 1;
   (e) contacting said hepatocyte with said supernatant; and
   (f) measuring the metabolic activity of said hepatocyte, wherein a decrease in metabolic activity in the presence of said supernatant compared to that in the absence of said supernatant indicates that said compound is toxic in vivo.

14. A method of neutralizing a toxic compound in a bodily fluid of a mammal, comprising contacting said fluid with the hepatocyte of claim 1 in vitro.

15. The method of claim 14, wherein said mammal is a human.

16. A method of evaluating the toxicity of a compound in vitro, comprising
   (a) providing a metabolically-active hepatocyte;
   (b) contacting said metabolically-active hepatocyte with said compound to generate a cell supernatant;
   (c) removing said cell supernatant from said metabolically-active hepatocyte;
   (d) providing the hepatocyte of claim 1;
   (e) contacting said hepatocyte with said supernatant; and
   (f) measuring the viability of said hepatocyte, wherein a decrease in viability in the presence of said supernatant compared to that in the absence of said supernatant indicates that said compound is toxic in vivo.

17. A method of evaluating the toxicity of a compound in vitro, comprising
   (a) providing the hepatocyte of claim 1;
   (b) contacting said hepatocyte with said compound; and
   (c) measuring the viability of said hepatocyte, wherein a decrease in viability in the presence of said compound compared to that in the absence of said compound indicates that said compound is toxic in vivo.

18. A method of evaluating the toxicity of a compound in vitro, comprising
   (a) providing the hepatocyte of claim 1;
   (b) contacting said hepatocyte with said compound; and
   (c) measuring the metabolic activity of said hepatocyte, wherein a decrease in metabolic activity in the presence of said compound compared to that in the absence of said compound indicates that said compound is toxic in vivo.

19. A perfusion device comprising
   (a) a housing defining a perfusion inlet and a perfusion outlet;
   (b) a porous membrane structure mounted within said housing to define a perfusion compartment and an adjacent hepatocyte compartment; and
   (c) virally-immortalized mammalian hepatocytes, said hepatocytes (1) being derived from a normal liver cell, (2) having differentiated hepatocyte-specific metabolic activity; and (3) having the ability to proliferate, wherein said hepatocyte is nontumorigenic after prolonged culture and wherein serum is not required for proliferation in prolonged culture.

* * * * *